Aug. 30, 1955 O. A. KRIETER Plant Pat. 1,413
ROSE PLANT
Filed May 22, 1953
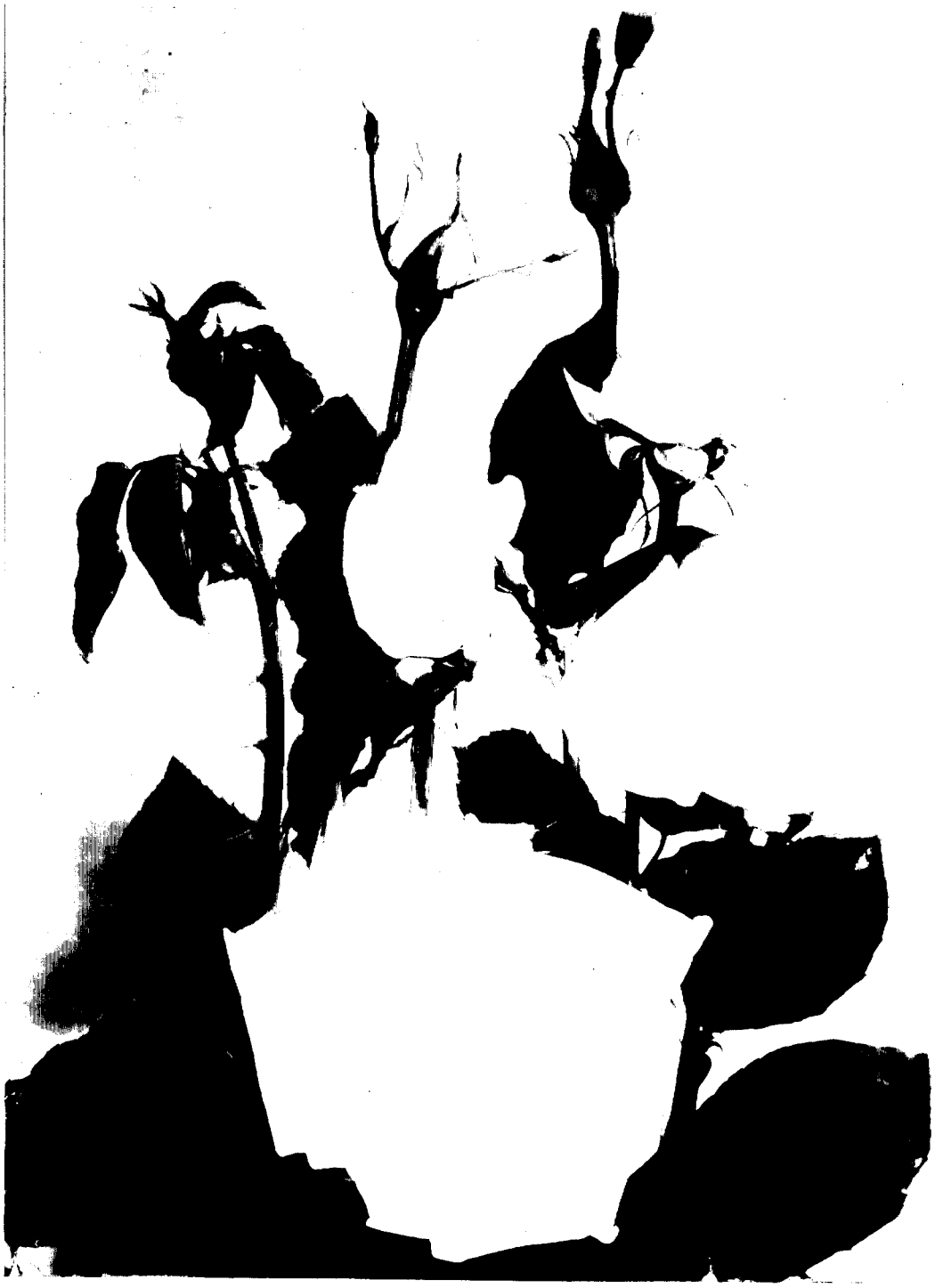
INVENTOR
Otto A. Krieter
By Orville M. Kile
Plant Pat. Agent United States Patent Office Plant Pat. 1,413
Patented Aug. 30, 1955

1,413

ROSE PLANT

Otto A. Krieter, Chicago, Ill., assignor to A. N. Pierson, Inc., Cromwell, Conn., and American Bulb Company, Chicago, Ill., jointly Application May 22, 1953, Serial No. 356,923

1 Claim. (Cl. 47—61)

My present discovery pertains to a new variety of hybrid tea rose plant in the class producing yellow blooms. It originated as a cultivated sport of Golden Rapture (unpatented) which I discovered in the greenhouse of the Angel Guardian Orphanage located in Chicago, Illinois, I asexually reproduced this new sport in these greenhouses by means of cuttings and also carried on growing tests and made observations to determine its qualities and commercial usefulness. It has also been reproduced asexually in Connecticut, and in both instances the resulting plants show the distinguishing characteristics of the original sport.

Unlike its parent, this new variety is uniform throughout the year in producing its clear yellow flowers of good marketable quality. Its abundant dark foliage is borne close to the flower and forms a pleasing contrasting frame for the flower.

Accompanying illustrations show several specimens of the flower, stem and foliage of this new variety in as near their true colors as the artist could show them, although it must be pointed out that in an effort to indicate shadows, the color is sometimes a little too intensified.

Following is a detailed description of my new variety, color terminology and plate numbers referring to Ridgway's Color Standards and Nomenclature:

THE PLANT

Growth: Vigorous; upright; medium heavy.
Form: Bush.
Blooming season: Recurrent; continuous.
Stems: Moderately heavy. Have many large, sharp thorns which are downward-pointing, greenish-white or red-tinged.
Foliage:
- *Quantity.*—Abundant.
- *Position.*—Well up toward bloom, and extending low on the stems.
- *Type.*—Pinnately compound, with 3 to 7 leaflets, the first below the peduncle being often a single leaflet.
- *Shape.*—Ovate, with rounded base and acuminate apex.
- *Size.*—Large, terminal leaflet 3 to 3½ inches long and 2 to 2¼ inches wide; laterals progressively much smaller.
- *Color.*—Mature foliage is dark green, between Dark Yellowish Green (Plate XVIII) and Empire Green (Plate XXXII), with under surface approximately Deep Malachite Green (Plate XVIII). New foliage red-tinged, with Russet-Vinaceous (Plate XXXIX) to Deep Hellebore Red (Plate XXXVIII). Later it becomes approximately Calliste Green (Plate VI), edged with Acajou Red (Plate XIII).
- *Edge.*—Sharply serrated; single.
- *Texture.*—Leathery and soft.
- *Aspect.*—Slightly dull; midrib prominent.

- *Rachis.*—Slender; upper surface grooved, under surface smooth; short.
- *Stipules.*—Medium length and width; clinging except for the long sharp points.

THE FLOWER

Bud:
- *Size.*—One inch long when sepals first break.
- *Form.*—Pointed at first, becoming ovoid.
- *Color.*—Small bud just beginning to open is approximately Greenish Yellow (Plate V), later becoming Straw Yellow to Amber Yellow (Plate XVI). Approximately Lemon Chrome (Plate IV) just before unfolding.
- *Sepals.*—Partly foliaceous, hooding above small bud. Color same as that of foliage.
- *Peduncle.*—Short (Usually 2½ to 4 inches long). Color approximately Biscay Green (Plate XVII). Covered with sharp spines. Erect and strong.
- *Opening.*—Very even.

Bloom:
- *Borne.*—Singly, on strong stems.
- *Size.*—Large, attaining 5 inches in diameter when grown under favorable conditions.
- *Form.*—Pointed, high-centered.
- *Quantity of bloom.*—Produces a large number of flowers per year.
- *Color.*—Uniformly clear, over-all yellow, with no white-streaked or whitish-colored flowers produced. The color of the opening rose is usually between Strontian Yellow (Plate XVI) and Lemon Chrome (Plate IV). There is some variation of color, with some of the blooms falling between Lemon Chrome and Apricot Yellow (Plate IV). Older flowers usually are between Empire Yellow (Plate IV) and Wax Yellow (Plate XVI), with edges of petals lightening to approximately Amber Yellow (Plate XVI).
- *Petalage.*—Double, with approximately 25 petals.
- *Fragrance.*—Intense and pleasing.
- *Longevity.*—Lasts exceptionally well, both on plant and as cut flower.

Petals:
- *Size.*—Outer petals 1½ inches wide by 1¾ inches long, on the larger flowers.
- *Shape.*—Obcordate to oval.
- *Color.*—Lemon Chrome (Plate IV) aiglet is more pronounced on inner surface. Blends upward into a lighter yellow, which is approximately Amber Yellow (Plate XVI) on the petal edges.
- *Texture.*—Leathery and substantial.

Reproductive organs:
- *Pistils.*—Many. Tightly grouped in center. Partly enclosed in ovary. Styles—even lengths; slender; exposed portion short; white with occasional slight red tinge near top. Stigmas—small, light yellow.
- *Stamens.*—Many, arising from outside pithy ring which surrounds pistils. Filaments—of uneven lengths; curved inward, bright yellow, approximately Light Cadmium (Plate IV), occasionally red-tinged. Anthers—meduim-sized; dark yellow, approximately Yellow Ochre (Plate XV).

COMPARISON

The variety most like my new variety is Golden Rapture (unpatented), but the chief differences are as follows:

1. In certain seasons of the year, under certain conditions of light and temperature, Golden Rapture produces a considerable quantity of yellowish white flowers unfit for commercial use, but my new variety produces substantially none of these whitish-colored flowers, even when grown under the same conditions. Since Golden Rapture averages approximately 25 percent of its flowers of the undesirable color, this makes a sharp difference between the two varieties.

2. The color of the flowers of my new variety is somewhat deeper, on a consistent average, than those of Golden Rapture in its normal color.

3. Although my variety is similar in growth to that of Golden Rapture, its wood is somewhat lighter in weight and the average of long stems is not quite so great as for Golden Rapture.

4. The size of the flower of my new variety averages larger.

5. The petalage of the flower of my variety averages greater.

Having thus disclosed my discovery, I claim:

The new and distinct variety of hybrid tea rose plant, substantially as herein shown and described, characterized particularly by its abundant green foliage; its large, well-formed, symmetrical flowers; the deep yellow color of its flowers; and the substantial uniformity of the yellow color of its flowers throughout the year and under all weather circumstances, as contrasted with a somewhat similar yellow variety that at certain seasons normally produces a large percentage of whitish, unsalable flowers.

No references cited.